United States Patent [19]

Pigache et al.

[11] Patent Number: 5,511,982
[45] Date of Patent: Apr. 30, 1996

[54] DEVICE FOR TESTING A PERSON'S ATTENTION

[75] Inventors: Robert Pigache, 43a Boulevard Clemenceau, F067000 Strasbourg, France; Lothar Ludwig, Kirchdorf, Germany

[73] Assignee: Robert Pigache, Tunbridge Wells, United Kingdom

[21] Appl. No.: 150,017

[22] PCT Filed: May 14, 1992

[86] PCT No.: PCT/EP92/01061

§ 371 Date: Nov. 15, 1993

§ 102(e) Date: Nov. 15, 1993

[87] PCT Pub. No.: WO92/20282

PCT Pub. Date: Nov. 26, 1992

[30] Foreign Application Priority Data

May 16, 1991 [EP] European Pat. Off. ............. 91107989

[51] Int. Cl.⁶ .................................................. G09B 3/00
[52] U.S. Cl. .................. 434/350; 434/236; 434/258; 128/746
[58] Field of Search .................. 434/236–238, 434/163, 258, 308, 307 R, 350, 342; 128/746

[56] References Cited

U.S. PATENT DOCUMENTS

| | | | |
|---|---|---|---|
| 3,685,169 | 8/1972 | Blau et al. | 434/342 |
| 3,690,020 | 9/1972 | McBratnie | 434/163 |
| 3,934,226 | 1/1976 | Stone et al. | 434/308 X |
| 4,024,499 | 5/1977 | Bosscher . | |
| 4,375,080 | 2/1983 | Barry et al. | 434/238 X |
| 4,464,121 | 8/1984 | Perelli | 434/258 X |
| 4,489,610 | 12/1984 | Slavin . | |
| 4,510,942 | 4/1985 | Miyamae et al. . | |
| 4,515,169 | 5/1985 | Ward . | |
| 4,556,069 | 12/1985 | Dalton, Jr. et al. . | |
| 4,730,253 | 3/1988 | Gordon . | |
| 4,789,235 | 12/1988 | Borah et al. | 434/236 X |
| 5,267,865 | 12/1993 | Lee et al. | 434/307 X |

FOREIGN PATENT DOCUMENTS

| | | |
|---|---|---|
| 2227264 | 12/1973 | Germany . |
| 2830297 | 1/1980 | Germany . |

OTHER PUBLICATIONS

"Comparison of Scoring Methods for Tests of Attention, Including an Error Index for Use With Schizophrenic Patients" by R. M. Pigache, *Perceptual and Motor Skills*, 1976, 42, 243–253.

*Primary Examiner*—Richard J. Apley
*Assistant Examiner*—Glenn E. Richman
*Attorney, Agent, or Firm*—Norbert P. Holler; Gottlieb, Rackman & Reisman

[57] ABSTRACT

In a device to test a person's attention or concentration ability, a series of digits is read out at a pre-determined, alterable speed by a speech recorder (62) and delivered by a speech generator (66) to headphones (10). The subject must press a button (16) every time a target (e.g. "0") is heard. Also every time a "0" is heard, a control unit (50) produces a window signal which is connected by an error logic circuit (70) to the key-press impulse. If the reaction is correct, the key-press impulse will be within the time window, and a counter (74) will accordingly increase the number of the "score". Any key-press impulse falling outside the time window is an omission error to be counted by another counter (75). The counter status is then analyzed to calculate an error index ($I^E$).

17 Claims, 3 Drawing Sheets

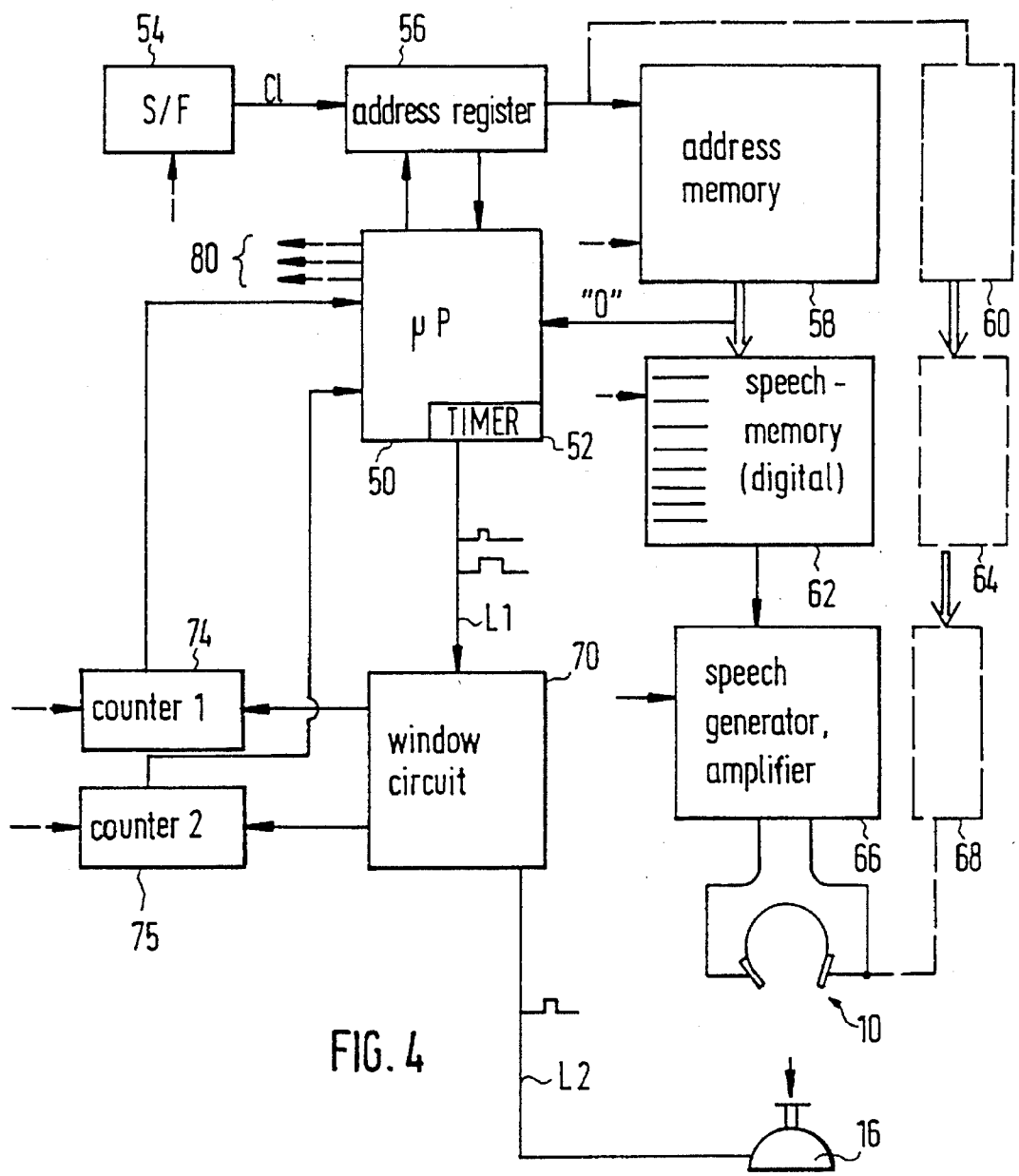
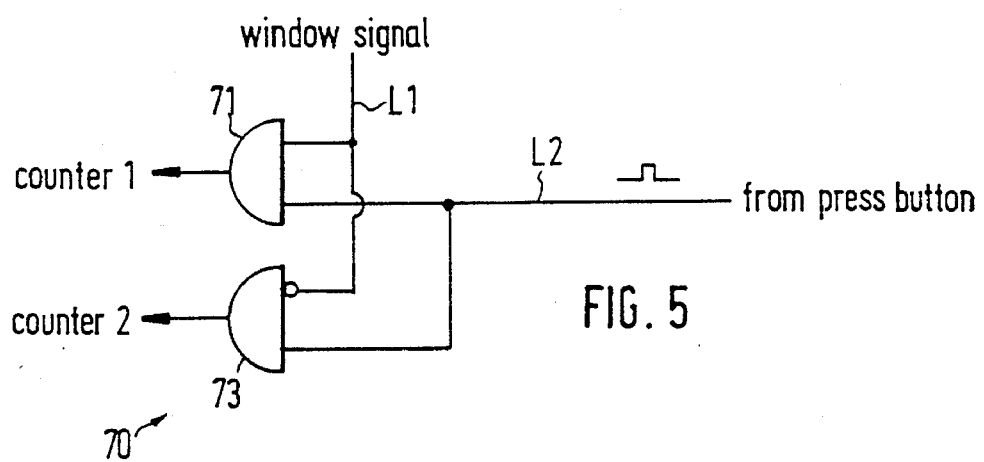

DEVICE FOR TESTING A PERSON'S ATTENTION

The invention concerns a device for testing a person's attention.

BACKGROUND OF THE INVENTION

Specific devices exist for different purposes concerning the testing of a person's attention or ability to concentrate. One such test was proposed by R. M. Pigache for patients suffering from schizophrenia (Perceptual and Motor Skills, 1976, 42, 243–253).

In this particular proposal, the person to be tested listens to strings of digits, letters, words or other sounds, and must react, for example, to particular digits, e.g. the digit "0", by pressing a button with the hand or foot. This test can be carried out so that there is a first phase during which the subject hears the same digits (stimuli) in both ears, then in the next test phase the stimuli are heard in differing order in the different ears, however the subject need only react to certain targets in the two ears (in the following example, this is the "0"), or in a designated ear when information to the other ear serves purely as a distracting signal. The series of stimuli can be delivered to the subject at differing speeds.

At present, however, the tests outlined above can only be carried out at considerable personnel cost. If, for example, nurses or medical technicians read the series of stimuli aloud to the subject, these members of staff must pay very great attention in order both to read out the series of stimuli at a constant speed and very clearly, and to watch very carefully whether the subject is reacting correctly to the targets or is reacting incorrectly where there is no target. The subject carrying our the test must receive appropriate instruction.

The conditions described above can lead to the test results being open to question in that the reproducibility of all tests cannot be guaranteed.

BRIEF DESCRIPTION OF THE INVENTION

An invention was needed to develop a device for the testing of a person's attention which could guarantee exact reproducibility of each test and which could also be run with the minimum of personnel cost yet produce precisely measurable results.

In view of this, the following features were proposed for the test device:
 a speech recording would be used to read stimuli at constant intervals;
 the stimuli would be produced from a speech generator and made audible to the subject through a loudspeaker or headphones,
 a key, a button, a toggle switch or the like should be pressed by the subject on recognition of a specific stimulus (target) which would produce a key impulse, and
 a recording device would register this impulse and correlate it both with the targets and other stimuli.

It was considered advisable to use digits as stimuli which meant that the digit "0" could be used as a target.

Using the device set up in the manner described above, it is possible to reproduce test conditions exactly for different subjects and/or at different times. This guarantees sound predictive results. The stimuli are stored in the speech recording in a pseudo-random order and can be read and heard according to a specific cycle frequency at specific time intervals. The subject presses a button every time he or she recognises a "0" and this button delivers a key impulse to the recorder. The recorder receives information not only from the key impulses but also information about the stimuli and targets. This allows the evaluation of individual tests to be carried out rapidly and effectively, enabling the tester to determine whether the subject has reacted correctly to the targets or has pressed the button when no target was heard.

To improve the reproducibility of the test conditions, it is helpful if an information speech recorder and/or a display is provided to deliver instructions to the subject about how to perform the test. It has of course been shown that keeping the subject informed, for example through a medical technician, is adequate in the single case but that these instructions differ from case to case and this can affect the measured results.

As suggested above, there is a quite simple test which involves identical stimuli being delivered to both of the subject's ears through headphones so that the subject must react each time he/she hears a "0". The reading of the series of digits by the speech recorder and the generation of acoustic information by the speech generator takes place at a specific frequency. This frequency can be altered. For preference, there will be two different reading speeds for the speech recorder, or speeds for other stimuli. At the faster speed the subject will hear two stimuli per second, at the slower speed the subject hears one stimulus every two seconds.

The type of operation described above can be called "mono operation". This is where "diotic stimuli" are delivered. In order to achieve better predictive measurable results, the invention also suggests the use of additional and alternative so-called dichotic stimuli. This means that separate channels will carry differents series of stimuli to the left and the right ears of the subject. The subject only reacts to targets which he perceives in one ear, while the stimuli to the other ear represent purely distracting sounds. In this case care is taken that a target cannot be heard by both ears at the same time.

In accordance with the invention, this variant of the test requires that the speech generator is fitted with two channels for the headphones and that the control device has a switch arrangement, through which either similar stimuli can be delivered simulataneously or different stimuli can be delivered to the different channels.

If these features are combined with a speed switch device, which allows the selection of several reading speeds for the stimuli, foru different basic test types can be achieved; first: diotic stimuli at slow speed; second: dichotic stimuli at slow speed; third: diotic stimuli at greater speed; fourth: dichotic stimuli at greater speed.

With such a device, four sub-tests can be carried out in sequence, each of which takes about five minutes. For example, in the first 5-minute phase, dichotic stimuli may be delivered to the subject at the faster speed. During the five minutes (=300 seconds) the subject hears in both ears simultaneously a total of 600 digits, within which are 50 noughts.

The best result msut therefore involve the subject in pressing the button immediately after he hears each nought, without pressing the button once for the other 550 non-nought stimuli. If the subject fails to react to a nought by pressing the button, the resultant error is called an omission error. If the subject reacts incorrectly by pressing the button without a nought being heard, the resultant error is called a commission error. This now requires definition of a criterion by which can be determined whether a key-press by the subject was a reaction to a heard nought or was an error. Thus the invented device provides a time control arrangement whereby a window signal of pre-determined duration follows each target delivery and a connector switch connects the window signal with the key-press. If the digit series is spoken slowly, e.g. at a rate of one digit per two seconds, the time span of the window signal will be four seconds. At the faster digit rate, the time span of the window signal is only 1.5 seconds. If the person to be tested waits so long to press the button that the window signal has disappeared, the key-press will be analyzed as a commission error.

The invention device in its simplest form is produced with the aid of a multitrack tape recorder. The first track holds a cycle signal, the second a series of digits, for example for the left channel, the third track holds a series of digits for the right channel and the fourth track holds a series of impulses which recognise the delivery of a "nought". The recording device can then be, for example, a polygraph, through which the frequency of signals and the target impulses are recorded, while a further track records the key-press impulse. The analysis of the recording can then be done manually or through an appropriate reading device. It will first be established whether the distance of a single key impulse is distanced within the maximum interval from a target impulse. Thus the omission and commission errors can be established. Analysis through a normal calculator then follows.

A counter is provided which can determine the ommission errors by counting each correct key-press impulse. Since the number of targets or noughts in a digit series is known, the number of omission errors can be determined by subtracting the counter total from the number of noughts.

A second counter counts key-press impulses which do not fall within the window signals. For a given number of stimuli and a given number of targets the difference can be calculated to show the number of non-targets. Thus the content of the second counter represents the commission errors.

For preference the device will be completely digital in its operation. In a read/white memory (RAM), speech signals will be held in digital form for the individual digits 0 to 9. In a further memory will be held the address signals for the speech recorder, and the address memory will be continuously addressed by an address register. The address memory will hold the addresses for the speech recorder already compiled in a pseudo-random order. Two channel instruments will require two address memories and speech recorders as well as two speech generators.

Analysis is carried out by a calculation programme which calculates an error index and other derived values from the recorded key-press impulses.

A preferred formula for the error index $I_E$ is:

$$I_E = O_m/n_1 + 2 \cdot C_o/(s-n_1) \quad (1)$$

$I_E$=eror index
$O_m$=ommission errors
$n_1$=number of targets
$c_o$=commission errors
s=total number of stimuli inc. $n_1$ The omission errors and commission errors are calculated in relation to the counter data as follows:

$$O_m = n_1 - <\text{counter 1}> \quad (2A)$$

$$C_o = <\text{counter 2}> \quad (2b)$$

Thus for a subtest which involves 600 dichotic stimuli with 50 targets read at fast speed, the following error index for 15 omission errors and 80 commission errors can be calculated:

$$I_E(F_2) = \frac{(50-35)}{50} + 2 \cdot \frac{80}{600-50} \quad (3)$$

It is then possible to put together the results from all four five-minutes subtests (fast/slow for diotic and dichotic stimuli) in order to calculate total results, for example for the above-mentioned error index.

However it is more powerfully predictive to analyse the result of each subtest separately and to work out the association of the error index $I_E$ determined for each subtest with the results of the other subtests.

The speech signals read on a pseudo-random basis from the speech recorder are processed further by a control unit designated as a speech generator; in particular they are demodulated (by delta modulated stored speech signals) and amplified, in order to be delivered over the headphones.

The total test run, which includes several subtests, is automatically controlled, by a control unit in charge of a time counter and which can run through a series of subtests each with differing parameters (diotic/dichotic stimuli; fast/slow).

The programme processes the key-press impulses registered during each subtest and the processed results are then associated with each other.

The digital version of this device has a speech recorder with a digital store (e.g. RAM) in which the individual stimuli corresponding to speech signals are stored either in an address or an address group so that the output of one address memory is connected with the address input of the speech recorder and so that the speech recorder addresses are stored in the address memory, which is progressively addressed through an address register, on a pseudo-random basis.

An impulse generator with switchable impulse frequency, to which the address register is connected, is used for the change from slow to fast digit series.

BRIEF DESCRIPTION OF THE DRAWINGS

In the following, with the help of diagrams, further details are given of the various ways in which the device can be used. They show.

DETAILED DESCRIPTION OF THE INVENTION

Figure 1:
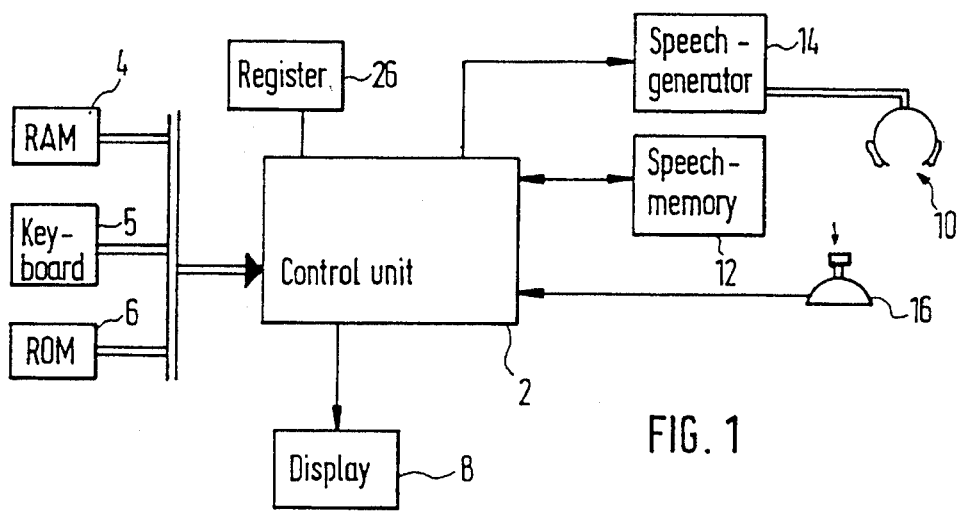
FIG. 1 a block diagram of a device for testing the attention and concentration ability of a person, FIG. 2 a schematic representation of apparatus for the generation of spoken digit series, FIG. 3 a sketch of a recording device in the form of a polygraph FIG. 4 a block diagram of a digital form of the invented device FIG. 5 a detailed wiring diagram of the error logic circuit shown in FIG. 4 as a block FIG. 6 a sketch which shows the connection between the spoken series of digits and the recording of different error types.

The block diagram shown in FIG. 1 shows a control unit which comprises a microprocessor, a microcomputer or similar device. Connected to the control unit 2 through a bus shown on the left of FIG. 1 are a read/write memory 4, a keyboard 5 and a read only memory(ROM) 6. In both memories 4 and 6 are stored programmes, data etc. for the operation of control unit 2. Through the keyboard 5, commands can be given to the control unit 2. A display 8 shows test results, but this can also be used to display instructions for the subject in preparations for a test.

Also connected to the control unit 2 is a speech recorder 12, in which digit series are stored. A speech generator 14 processes the signals from the speech recorder 12 in order to convert them into low frequency signals for the two channels to be delivered through both headphones 10.

In the simplest example, the speech recorder 12 is set up as a multi-track tape recorder.

Figure 2:
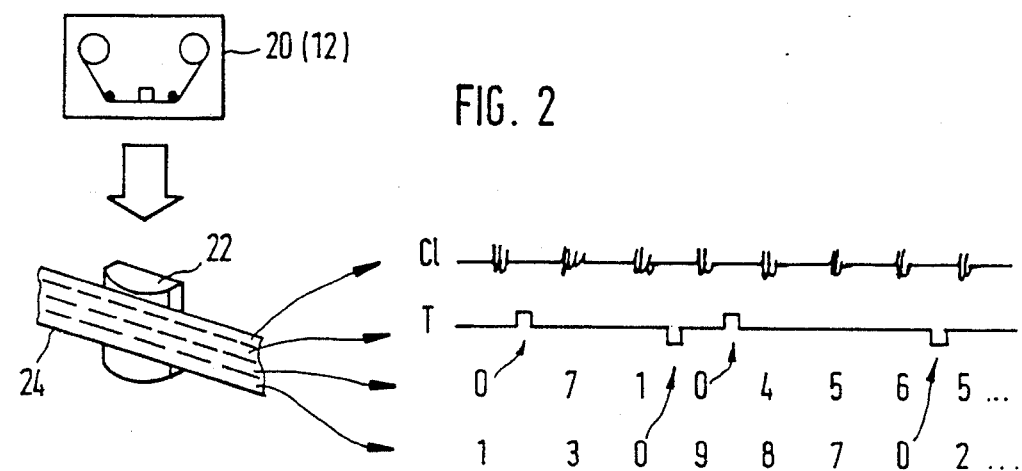

FIG. 2 shows in schematic form a tape cassette 20, a multi-track audio film head 22 and a four-track tape 24 played along it. On the upper track a cycle signal C1 is stored in the form of a high frequency signal burst.

On the second track the so-called target impulses are stored which specify where in the third or fourth track there is a nought stored. The polarity corresponds to the individual target impulse T.

In the third track the digit series 0,7,1 . . . is stored, while in the fourth track the digit series 1,3,0,9 . . . is stored.

The control unit 2 represented in FIG. 1 controls the operation of the tape, i.e., of the speech recorder 12. The digit series is given over both channels of the headphones 10 via the speech generator 14 (which for example comprises an amplifier). The subject wearing the headphones 10 hears in the left ear, for example, the digit series 0,7,1 . . . from the third track and in the right ear hears the digit series 1,3,0,9 . . . from the fourth track. According to the instructions given in advance, only the digit series 0,1,2,0 heard in the left ear is "relevant" while the digit series heard in the right ear will serve only as a distraction. Each time the subject hears a "0" in the left ear he or she must press button 16, which then delivers a key-press impulse to the control unit 2. The control unit 2 then gives the corresponding signal impulse to the recording unit 26.

Figure 3:
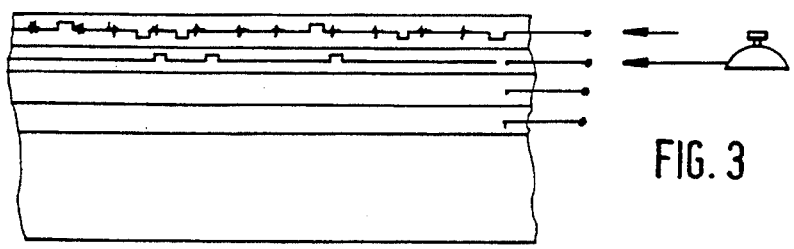

The recording unit 26 can be a polygraph, as shown in FIG. 3. While the cycle signal Cl and the target impulse T are stored together in the upper channel, in the second channel registers the key-press impulse. Either through automatic or manual analysis it can be established whether there was a key-press impulse delivered on a target impulse (polarity!) relevant for the channel within a specific time interval. In this way the number of omission errors and commission errors can be determined.

In many respects a more comfortable form of the equipment roughly sketched in FIG. 1 is shown in FIG. 4. The whole device works digitally.

A microprocessor 50 works together with a timer 52 to control different circuits which are described in more detail below. Control is achieved with the aid of an operating programme which is stored in the ROM 6 and/or RAM 4 shown in FIG. 1 (omitted in FIG. 4 ).

In FIG. 4 control signal ends to individual blocks are shown with dotted lines. These come from the control signal outputs 80 from the microprocessor 50.

An impulse generator 54 capable of switching between a high and a low impulse frequency delivers a cycle impulse C1 to the address register 56. If this is started from the microcomputer 50, it addresses consecutive storage locations in an address store 58. Addresses from a digital speech recorder 62 are stored in the address store 58 on a previously determined pseudo-random basis. The speech signals (digits) are stored delta-modulated and for each digit a field or an address or an address group is read from the speech recorder so that this address group is established from the output signal of the address store 58. When a "0" is read out, this will be signalled to the microprocessor 50 which immediately gives a window signal over the timer 52 to a circuit L1. Depending on whether the digit series is read out fast or slow (the frequency of the cycle signal Cl), the window signal will last either four seconds or 1.5 seconds.

From the speech recorder the signals for each digit pass into a speech generator 66, which will comprise, for example, a demodulator circuit and an amplifier. For the mono operation (diotic stimuli), the single digit will then be heard over both headphones 10. The subject hears the series of digits and presses the button 16 for every "0" so that a key-press impulse is given over a circuit L2 to an error logic and window circuit 70. The latter circuit also receives the window signal from the microcomputer 50 over the circuit L1.

FIG. 5 shows a possible hardware system for the switch unit 70. The window signal is put together with the key-press signal on an add-link 71. In addition the inverted window signal goes to another add-link 73 from the circuit L1, as does the key-press signal from the circuit L2.

According to FIG. 4, a counter 1 is connected to the add-link 71, while a counter 2 is connected to the add-link 73.

If the subject reacts quickly enough, the key-press impulse in response to the heard "0" comes over the circuit L2 to the add-link 71 as long as the window signal is shown. This will produce an impulse at the output of the add-link 71 through which the counter 74 (counter 1) will be increased by one unit.

Given a known number of noughts per test series, the number of omission errors can be calculated by subtracting the counter status 74 from the number of targets.

The contents of counter 75 (counter 2) comprises the number of key-press impulses which have been produced outside all the window signals. This gives the number of commission errors.

By switching the frequency of the cycle signal Cl from the impulse generator 54, fast and slow series of digits (stimuli) can be produced.

A further variant is then achieved by delivering different series of digits to both headphones 10, as shown schematically in FIG. 2. For this certain additional components must be added to the set-up in FIG. 4, namely an additional address memory 60, an additional speech recorder 64 and an additional speech generator 68.

Figure 6:
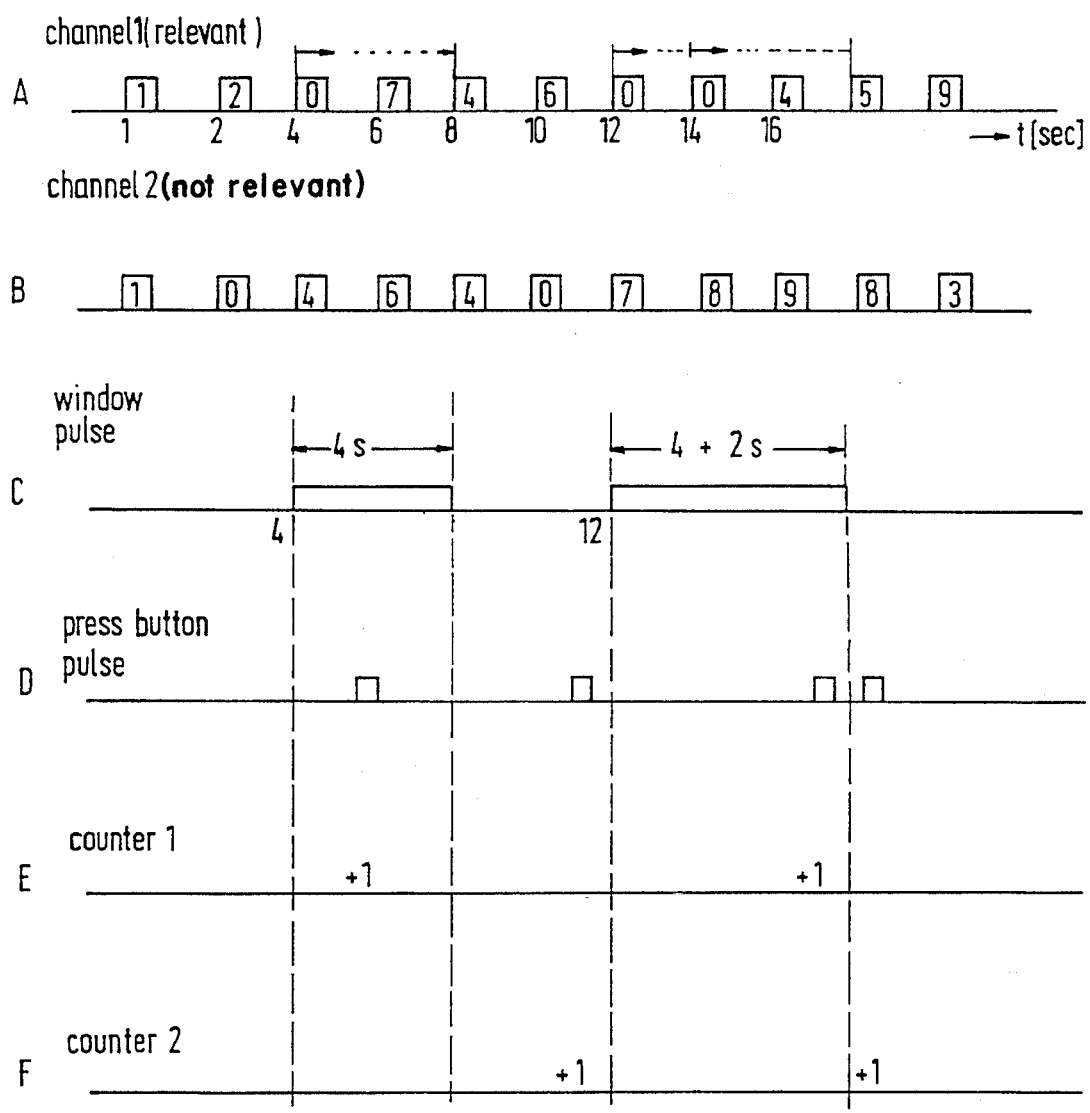

The analysis of counter status on counters 74 and 75 with the stored values for the total number of stimuli and the total number of targets takes place within the microprocessor according to a particular analysis programme. Thus for each subtest, which lasts five minutes, there is a calculation of the error index $I_E$ (formula 1) and following on from the individual error indices $I_E$ for the individual subtests, there is a further calculation in order to provide evidence of the concentration ability of the subject. FIG. 6 shows through an impulse diagram an example of the recording of errors.

In FIG. 6A and FIG. 6B the spoken digit series for one channel 1 and another channel 2 are represented. For example, the subject may have to listen to the digit series from channel 1 in the left ear and ignore the digit series heard from channel 2 in the right ear. The digit series are constructed so that no more than three noughts can be presented one after another, and a nought cannot be delivered through both channels at the same time.

FIGS. 6A and 6B illustrate the digit series for a "slow test" with dichotic stimuli (different digit series to both ears). A digit will be read out every two seconds. Every time a nought is spoken, the microprocessor 50 will produce a window signal lasting for four seconds (FIG. 6C).

If the subject now presses the button 16 within the duration of the window impulse, then a key-press impulse is produced as in FIG. 6D. The conjunction of the key-press impulse with the window impulse will—as described above—produce a signal which raises the value of the counter 1 by 1 unit.

As shown in the middle of FIG. 6 by D, the subject presses the button 16 although there has been no nought spoken in the "relevant" channel 1. The keypress impulse shown in the middle of FIG. 6D represents a commission error, probably caused by the nought spoken in the "not relevant" channel 2 shortly before.

According to FIG. 6A noughts were spoken at time points 12s and 14s. At time points 12s, i.e. at time the first nought is spoken, the provision of a window impulse is activated. This window impulse would last four seconds by itself. Since, however, at time point 14s a further nought is spoken, the window signal is extended by a further four seconds, which gives a combined window signal lasting for six seconds.

According to FIG. 6D it should be noted that the button was pressed twice in reaction to the two noughts and the first of theses presses was correctly timed during the window impulse, but the second time it was too late, being outside the window impulse. At the first key-press impulse, counter 1 increased, at the second key-press impulse counter 2 increased, and this also increased according to FIG. 6D at the middle key-press impulse.

Thus, according to FIG. 6, the subject recognised a total of three noughts in channel 1 in this time segment, two of which were correct, so that counter 1 increased twice. Once the nought in channel 2 was falsely recognised as being in the "relevant" channel. This is recorded, like the delayed key-press in connection with the second window signal, as a commission error.

The examples described above could be modified in many ways. So, by way of example, some of the above have been explained and some of the elements represented schematically in FIG. 4 can also be achieved through appropriate software characteristics.

We claim:

1. Device for testing a person's attention, comprising:

speech memory means for generating stimuli, and means for reading said stimuli out at simultaneous time intervals from said speech memory means;

auditory stimulus generator means for rendering said stimuli audible to the person being tested and including loud-speaker or headphone means providing two channels for separate transmissions of sounds to the ears of said person, and a control unit including a switch unit by means of which either the same or different stimuli can be produced in the two channels;

key-press means adapted to be operated by the person being tested upon recognition of a specified target stimulus for delivering a corresponding key-press impulse;

recording means for sensing said key-press impulse and correlating the same with said target stimuli as well as with such stimuli as are different from said target stimuli; and time control means for producing time window signals of predetermined time intervals at each delivery of a target stimulus, and gating circuit means for combining said time window signals with said key-press impulses.

2. The device of claim 1, wherein said stimuli are digits of which the digit "0" serves as a target stimulus.

3. The device of claim 1, wherein said stimuli are letters and/or words and/or sounds of different frequency.

4. The device of claim 1, 2 or 3, wherein means for informing the person to be tested of necessary information to carry out the test are provided, said informing means comprising an information speed recorder and/or a display.

5. The device of claim 4, wherein said means adapted to be operated by said person to be tested comprises a key, a button or a toggle switch or a lever.

6. The device of claim 1, wherein a speed switch unit is provided for enabling any one of several presentation speeds to be selected for said stimuli.

7. The device of claim 1, further comprising a first counter for counting every key-press impulse which coincides with a time window signal.

8. The device of claim 7, further comprising a second counter for counting each key-press impulse which does not coincide with a time window signal.

9. The device of claim 1 or 8, wherein said control unit incorporates a programme which calculates an error index ($I_E$) from recorded key-press impulses and also calculates further derived values.

10. The device of claim 9, wherein said control unit comprises a time counter and automatically runs a series of subtests with different parameters.

11. The device of claim 10, wherein said programme establishes means for processing recorded key-press impulses and for obtaining results therefrom for each of the subtests individually and means for subsequently correlating the processed results with each other.

12. The device of claim 11, wherein said speech memory means comprises a digital memory in which the individual stimuli for particular key-press signals are recorded and stored under either an address or an address group, and an address memory which has an output thereof connected to an address input of said speech memory means, said speech or stimulus memory addresses being stored on a pseudo-random basis in the progressively addressed address memory through an address register.

13. The device of claim 12, further comprising a clock generator with switchable cycle frequency, said address register being connected to said clock generator.

14. The device of claim 1, wherein said means adapted to be operated by said person to be tested comprises a key, a button or a toggle switch or a lever.

15. The device of claim 14, wherein said control unit incorporates a programme which calculates an error index ($I_E$) from recorded key-press impulses and also calculates further derived values.

16. The device of claim 1, wherein said speech memory means comprises a digital memory in which the individual stimuli for particular key-press signals are recorded and stored under either an address or an address group, and an address memory which has an output thereof connected to an address input of said speech memory means, said speech or stimulus memory addresses being stored on a pseudo-random basis in the progressively addressed address memory through an address register..

17. The device of claim 16, further comprising a clock generator with switchable cycle frequency, said address register being connected to said clock generator.

* * * * *

UNITED STATES PATENT AND TRADEMARK OFFICE
CERTIFICATE OF CORRECTION

PATENT NO. : 5,511,982

DATED : April 30, 1996

INVENTOR(S) : Robert Pigache et al.

It is certified that error appears in the above-identified patent and that said Letters Patent is hereby corrected as shown below:

On the title page, in the left-hand column, at item [75], for "43a Boulevard Clemenceau, F067000 Strasbourg, France" read — 7 Shepherds Walk, Tunbridge Wells, Kent TN2 3QR, United Kingdom —.

Signed and Sealed this

Seventeenth Day of September, 1996

*Attest:*

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,511,982
DATED : April 30, 1996
INVENTOR(S) : Robert Pigache et al.

It is certified that error appears in the above-identified patent and that said Letters Patent is hereby corrected as shown below:

On the title page, in the left-hand column, at item [73], for "Robert Pigache, Tunbridge Wells, United Kingdom" read — Psychometric Investments NV, Curacao, Netherlands Antilles —.

Signed and Sealed this

Nineteenth Day of November, 1996

Attest:

BRUCE LEHMAN

Attesting Officer

Commissioner of Patents and Trademarks